United States Patent
Shukla et al.

(10) Patent No.: US 8,263,750 B2
(45) Date of Patent: Sep. 11, 2012

(54) METHOD FOR PURIFYING A PROTEIN USING PROTEIN-A AFFINITY CHROMATOGRAPHY USING AN INTERMEDIATE WASH STEP

(75) Inventors: Abhinav A. Shukla, Manlius, NY (US); Peter Hinckley, Seattle, WA (US)

(73) Assignee: Amgen Inc., Thousand Oaks, CA (US)

( * ) Notice: Subject to any disclaimer, the term of this patent is extended or adjusted under 35 U.S.C. 154(b) by 528 days.

(21) Appl. No.: 12/225,216

(22) PCT Filed: Mar. 16, 2007

(86) PCT No.: PCT/US2007/006688
§ 371 (c)(1),
(2), (4) Date: May 18, 2009

(87) PCT Pub. No.: WO2007/109163
PCT Pub. Date: Sep. 27, 2007

(65) Prior Publication Data
US 2009/0306351 A1     Dec. 10, 2009

Related U.S. Application Data

(60) Provisional application No. 60/782,942, filed on Mar. 16, 2006.

(51) Int. Cl.
*A23J 1/00* (2006.01)
*C12P 21/04* (2006.01)
(52) U.S. Cl. .................................. 530/412; 435/70.1
(58) Field of Classification Search .................. None
See application file for complete search history.

(56) References Cited

U.S. PATENT DOCUMENTS

| 4,841,024 | A | * | 6/1989 | Nathans et al. ............ 530/388.1 |
| 6,127,526 | A | | 10/2000 | Blank |
| 6,333,398 | B1 | | 12/2001 | Blank |
| 6,870,034 | B2 | | 3/2005 | Breece et al. |
| 2003/0153735 | A1 | * | 8/2003 | Breece et al. ................. 530/413 |
| 2004/0229330 | A1 | | 11/2004 | Bettencourt et al. |

OTHER PUBLICATIONS

Bhuyan, A., "Protein stabilization by urea and guanidine hydrochloride," *Biochem.*, 41:13386-13394, 2002.
Gagnon, Pete, "Purification Tools for Monoclonal Antibodies," Validated Biosystems, Inc., Tucson, AZ, 1996, pp. 155-198; pp. 221-224.
Iyer et al., "Considerations during development of a protein A-based antibody purification process," *BioPharm*, pp. 14-20 and 53, Jan. 2002.
Schuler and Reinacher, "Development and optimization of a single-step procedure using protein A affinity chromatography to isolate murine IgG$_1$ monoclonal antibodies from hybridoma supernatants," *J. Chromatography*, 587:61-70, 1991.
Shukla et al., Structural characteristics of low-molecular-mass displacers for cation-exchange chromatography II. Role of the stationary phase, *J. Chromatography*, 827:295-310, 1998.
van Sommeren et al., "Effects of temperature, flow rate and composition of binding buffer on adsorption of mouse monoclonal IgG$_1$ antibodies to protein a sepharose 4 fast flow," *Preparative Biochem.*, 22(2):135-149, 1992.

* cited by examiner

*Primary Examiner* — Alexander Kim
(74) *Attorney, Agent, or Firm* — Susan E. Lingenfelter

(57) ABSTRACT

A method for purifying a protein using Protein A chromatography comprising a) absorbing the protein to Protein A immobilized on a solid support; b) removing contaminants by washing the immobilized Protein A containing the absorbed protein with a buffer comprising one or more chaotropic agents in combination with one or more hydrophobic modifiers and having a pH of at least 7.0; and c) eluting the protein from the Protein A immobilized on the solid support.

5 Claims, 1 Drawing Sheet

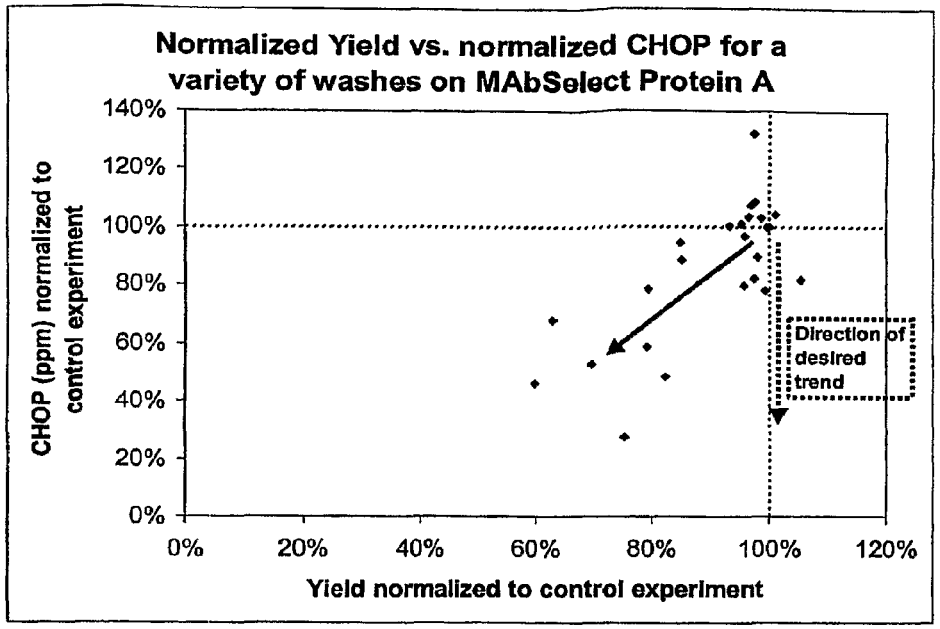
Figure 1a: Plot of normalized yield vs. normalized CHOP with various intermediate washes during Protein A chromatography on MAbSelect®.
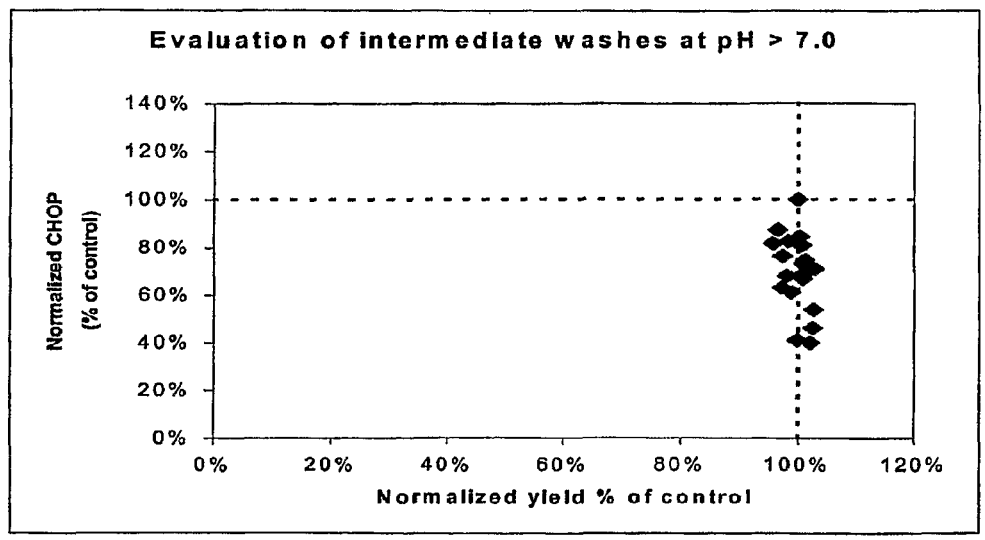
Figure 1b: Plot of normalized yield vs. normalized CHOP with various intermediate washes during Protein A chromatography on MAbSelect®.

METHOD FOR PURIFYING A PROTEIN USING PROTEIN-A AFFINITY CHROMATOGRAPHY USING AN INTERMEDIATE WASH STEP

CROSS-REFERENCE TO RELATED APPLICATIONS

This application is a national application under 35 U.S.C. §371 of International Application No. PCT/US2007/006688, having an international filing date of Mar. 16, 2007; which claims priority of provisional application U.S. Ser. No. 60/782,942, filed Mar. 16, 2006, the entire disclosure of which is relied upon and incorporated by reference.

FIELD OF INVENTION

The present invention relates to the field of protein purification using Protein A immobilized to a solid support. In particular, the invention relates to wash buffer formulations and method of using the wash buffers to remove host cell contaminants during the intermediate wash step, minimizing loss of the desired protein product. These wash buffer formulations also work well with different types of proteins.

BACKGROUND OF THE INVENTION

Protein A chromatography is widely employed for the preparative purification of proteins possessing a heavy chain Fc region comprising the $C_H2$ and $C_H3$ domains of an immunoglobulin molecule. (Vola et al. *Cell Biophys.* 24-25: 27-36, 1994; Gagnon, Protein A affinity chromatography, In: Purification tools for monoclonal antibodies, 1996, Validated Biosystems, Tucson, Ariz., 1996; Aybay and Imir, *J. Immunol. Methods* 233(1-2): 77-81, 2000; Ford et al., *J. Chromatogr. B* 754: 427-435, 2001; Fahrner et al, *Biotechnology and Genetic Engineering News*, 18: 301-327, 2001). Such Fc proteins include antibodies, particularly monoclonal antibodies, as well as Fc fusion proteins. Such proteins are typically produced by mammalian or bacterial cells engineered to express the desired recombinant protein, intracellularly or directly, into the culture medium or intracellularly. Purification of the expressed proteins typically begins with either collecting the cell culture medium to harvest extracellularly expressed protein or harvesting and lysing the host cells to release intracellularly expressed protein. This host cell "harvest medium" contains not only the protein of interest but also DNA, RNA, and protein contaminants from the host cell that must be separated from the desired protein. These host cell contaminants may be separated by various chromatographic methods based on their charge, size or hydrophobicity. The affinity of immunoglobulin heavy chain Fc regions for the IgG binding domains of Protein A allows for the direct capture and purification of such Fc proteins from complex host cell harvest medium that may contain many different host cell contaminants. Despite the high specificity of the Fc region for Protein A, host cell protein contaminants may still be present at varying levels in the final column eluate, thereby reducing the purity of the of the final protein product. To be useful for human therapeutic purposes, protein products must be separated from all of the extraneous media components and cell by-products, creating a need for purification methods that can maintain product yield while reducing host cell contaminant levels.

Typically Protein A affinity chromatography consists of a column comprising Protein A immobilized on to a solid support and equilibrated to a neutral pH. Cell culture harvest medium containing the desired protein product in addition to host cell contaminants is loaded directly onto the Protein A column followed by a preliminary wash with an equilibration buffer at an intermediate pH to remove any host cell contaminants that were not bound to the protein product of interest or the Protein A matrix. This is followed by an intermediate wash step to remove any bound host cell protein contaminants. As described below, such contaminants may bind to the Protein A matrix and/or to the protein of interest. The formulation of the intermediate wash buffer is typically similar to the elution buffer, except for having a more intermediate pH in place of the lower pH of the elution buffer. Following the intermediate wash step the protein product is then eluted from the Protein A column using an elution buffer.

For large-scale purification much effort is placed on optimizing the formulations of wash and elution buffers to maximize product yield. However, in a production situation where many different protein products are being purified at the same time, developing a unique wash buffer for each individual protein product requires significant time and resources to screen various buffer formulations to determine an appropriate wash buffer for each particular protein product. A "generic" intermediate wash buffer that could be used effectively with different types of proteins would be useful and desirable. A common path taken when designing wash buffers is to mimic elution buffer formulations but within an intermediate pH range. However, since elution buffer formulations are designed to maximize the recovery of a particular protein product these formulations are typically protein-specific and not easily transferred from one protein to another and typically are at lower pH, increasing the possibility of loss of product during the wash step due to weakening of the interaction between the protein product and the Protein A. Therefore, the formulation of the intermediate wash buffer should maintain a balance between contaminant removal and loss of protein product. Thus, it would be desirable to develop a "generic" wash buffer that could be used over a broad range of protein products, such as monoclonal antibodies and Fc-fusion proteins, that would maximize removal of host cell protein contaminants while minimizing loss of protein product during Protein A affinity chromatography.

The present invention provides a method of protein purification using such wash buffer formulations.

SUMMARY OF THE INVENTION

Within certain embodiments the invention provides method for purifying a protein from a solution containing at least one contaminant by Protein A chromatography comprising absorbing the protein to Protein A immobilized on a solid support; removing contaminants by washing the immobilized Protein A containing the absorbed protein with a buffer comprising one or more chaotropic agents in combination with one or more hydrophobic modifiers and having a pH of at least 7.0; and eluting the protein from the Protein A immobilized on the solid support.

Within the present invention are buffers including phosphate buffer, Tris buffer, acetate buffer and citrate buffer. The invention also includes pH ranges of between 7.0 to about 10.0, about 8.0 to about 10.0 and from about 9.0 to about 10.0

Within certain embodiments chaotropic agents are selected from urea, sodium thiocynate, and guanidinium hydrochloride and hydrophobic modifiers are selected from organic solvents including ethanol, methanol, isopropanol; alkyl glycols including ethylene glycol; propylene glycol; hexaethylene glycol; and detergents including polysorbates.

Within further embodiments the buffer comprises an agent that reduces electrostatic interactions including salts such as sodium salts, potassium salts, ammonium salts, citrate salts, calcium salts and magnesium salts.

Within other embodiments contaminants are Chinese Hamster Ovary cell proteins, solid support is agarose and proteins are antibodies or antibody fragment comprising at least the CH2 and CH3 domains and Fc-fusion proteins.

Within yet other embodiments are provided a method for purifying a protein from a contaminated solution by Protein A chromatography comprising absorbing the protein to Protein A immobilized on a solid support, removing contaminants by washing the immobilized Protein A containing the absorbed protein with a wash buffer comprising about 10% isopropanol and about 1M to about 3M urea and having a pH of about 9.0; and eluting the protein from the Protein A immobilized on the solid support. Such methods include methods wherein the wash buffer comprises about 10% isopropanol and about 1M to about 3M urea and having a pH of about 9.0. Methods where the buffer comprises 2M urea and 500 mM sodium thiocynate; methods where the buffer comprises 2M urea and 10% propylene glycol; methods where the buffer comprises 10% isopropanol and 1M to 3M urea and 1% Tween 80; methods where the buffer comprises 2M urea and 1% Tween 80.

These and other aspects of the invention will become evident upon reference to the following detailed description.

BRIEF DESCRIPTION OF THE DRAWINGS

FIGS. 1a and 1b show plots of normalized yield vs. normalized CHOP with various intermediate washes during Protein A chromatography on MAbSelect®.

DETAILED DESCRIPTION OF INVENTION

As used herein, "affinity chromatography" is a chromatographic method that makes use of the specific, reversible interactions between biomolecules rather than general properties of the biomolecule such as isoelectric point, hydrophobicity, or size, to effect chromatographic separation. "Protein A affinity chromatography" or "Protein A chromatography" refers to a specific affinity chromatographic method that makes use of the affinity of the IgG binding domains of Protein A for the Fc portion of an immunoglobulin molecule. This Fc portion comprises human or animal immunoglobulin constant domains $C_H2$ and $C_H3$ or immunoglobulin domains substantially similar to these. Protein A encompasses native protein from the cell wall of *Staphylococcus aureas*, Protein A produced by recombinant or synthetic methods, and variants that retain the ability to bind to an Fc region. In practice, Protein A chromatography involves using Protein A immobilized to a solid support. See Gagnon, *Protein A Affinity Chromotography*, Purification Tools for Monoclonal Antibodies, pp. 155-198, Validated Biosystems, 1996. Protein G and Protein LG may also be used for affinity chromotography. The solid support is a non-aqueous matrix onto which Protein A adheres. Such supports include agarose, sepharose, glass, silica, polystyrene, collodion charcoal, sand, and any other suitable material. Such materials are well known in the art. Any suitable method can be used to affix the second protein to the solid support. Methods for affixing proteins to suitable solid supports are well known in the art. See e.g. Ostrove, in Guide to Protein Purification, Methods in Enzymology, 182: 357-371, 1990. Such solid supports, with and without immobilized Protein A, are readily available from many commercial sources including such as Vector Laboratory (Burlingame, Calif.), Santa Cruz Biotechnology (Santa Cruz, Calif.), BioRad (Hercules, Calif.), Amersham Biosciences (part of GE Healthcare, Uppsala, Sweden) and Millipore (Billerica, Mass.). Protein A immobilized to a pore glass matrix is commercially available as PROSEP®-A (Millipore). The solid phase may also be an agarose-based matrix. Protein A immobilized on a agarose matrix is commercially available as Mab-Selec™ (Amersham Biosciences).

"Antibody" includes reference to both glycosylated and non-glycosylated immunoglobulins of any isotype or subclass, including human, humanized, chimeric, multi-specific, monoclonal, polyclonal, and oligomers thereof, irrespective of whether such antibodies are produced, in whole or in part, via immunization, through recombinant technology, by way of in vitro synthetic means, or otherwise. Thus, the term "antibody" is inclusive of, but not limited to, those that are prepared, expressed, created or isolated by recombinant means, such as (a) antibodies isolated from an animal (e.g., a mouse) that is transgenic for human immunoglobulin genes or a hybridoma prepared there from, (b) antibodies isolated from a host cell transfected to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences. Such antibodies have variable and constant regions derived from germline immunoglobulin sequences of two distinct species of animals. In certain embodiments, however, such antibodies can be subjected to in vitro mutagenesis (or, when an animal transgenic for human immunoglobulin sequences is used, in vivo somatic mutagenesis) and thus the amino acid sequences of the $V_H$ and $V_L$ regions of the antibodies are sequences that, while derived from and related to the germline $V_H$ and $V_L$ sequences of a particular species (e.g., human), may not naturally exist within that species' antibody germline repertoire in vivo. Also included are chimeric antibodies in which a portion of the antibody is homologous to a sequence of a particular species or a particular antibody class, while another portion of the antibody is homologous to a sequence of a different species or antibody class. See, e.g., U.S. Pat. No. 4,816,567 and Morrison et al., *Proc. Natl. Acad. Sci. USA,* 81:6851-6855, 1985). An antibody may have one or more binding sites. If there is more than one binding site, the binding sites may be identical to one another or may be different. For instance, a naturally occurring immunoglobulin has two identical binding sites; a single-chain antibody or Fab fragment has one binding site, while a "bispecific" or "bifunctional" antibody has two different binding sites.

"Fc fusion proteins" are recombinant fusion proteins comprising part or all of two or more proteins, one of which is an Fc portion of an immunoglobulin molecule, that are not fused in their natural state. Examples of such Fc fusion proteins include, but are not limited to, human receptor activator of NF-KappaB fused to an Fc portion of an immunoglobulin molecule (huRANK:Fc), tunica internal endothelial cell kinase-delta fused to an Fc portion of an immunoglobulin molecule (TEKdelta:Fc) and tumor necrosis factor receptor fused to an Fe portion of an immunoglobulin molecule (TNFR:Fc).

A solution containing at least one "contaminant" refers to a solution containing the protein product of interest as well as at least one or more foreign or objectionable molecules, particularly biological macromolecules such as DNA, RNA, or proteins. Such contaminants, which include "host cell protein contaminants", are any such foreign or objectionable molecules. Such contaminated solutions are usually obtained, for example, when host cells transfected to express the protein of interest are harvested and processed for protein purification. An exemplary host cell is the Chinese Hamster Ovary cell. Host cell protein contaminants from such cells are known by the acronym "CHOP" (Chinese Hamster Ovary cell Proteins). It is desirable to reduce the level of such contaminants in the final purified protein product. Contaminants may be detected and quantified by any appropriate method such as gel electrophoresis and staining, protein quantification assays such as ELISA, and DNA quantification assays such as those employing the polymerase chain reaction.

The terms "peptide," "polypeptide" and "protein" are used interchangeably throughout and refer to a molecule comprising two or more amino acid residues joined to each other by peptide bonds. The terms "peptide", "polypeptide" and "protein" are also inclusive of modifications including, but not limited to, glycosylation, lipid attachment, sulfation, γ-carboxylation of glutamic acid residues, hydroxylation and ADP-ribosylation.

To "purify" a protein means to reduce the amount of foreign or objectionable elements, in particular, biological macromolecules such as proteins, DNA or RNA that may be present in a sample of the protein. One method used to purify desired protein products is affinity chromatography, where the protein of interest is separated from undesirable elements by separating the desired protein product based on its affinity for a capture agent affixed to a support. The presence of foreign proteins in the purified product may be assayed by any appropriate method including gel electrophoresis and staining and by protein quantification assays such as ELISA. The presence of DNA may be assayed by any appropriate method including gel electrophoresis and staining and by DNA quantification assays employing polymerase chain reaction.

Unless otherwise noted, the terms "a" or "an" are to be construed as meaning "at least one of".

All documents, or portions of documents, cited in this application, including but not limited to patents, patent applications, articles, books, and treatises, are hereby expressly incorporated by reference.

The present invention relates to a method of purifying proteins using Protein A affinity chromotography having as part of the purification method an intermediate wash step employing a buffer formulated as described herein at a high pH buffer (>pH 7) and comprising at least one chaotropic agent and one hydrophobic modifier that selectively washes out host cell protein impurities while minimizing impact on product yield. Such intermediate wash buffer formulations were found to be effective for a range of antibodies and Fc fusion proteins. Incorporation of such a wash buffer into the intermediate wash step during Protein A chromatography will enable further templating of process conditions across monoclonal antibodies for this unit operation.

The invention provides a method for purifying a protein from a contaminated solution by Protein A chromatography comprising absorbing the protein to Protein A immobilized on a solid support; removing contaminants by washing the immobilized Protein A containing the absorbed protein with a wash buffer comprising a chaotrope and other additives including detergents, salts, solvents, and/or polymers, the buffer having a pH of at least 7.0; and eluting the protein from the Protein A. Within certain embodiments the invention provides method for purifying a protein from a solution containing at least one contaminant by Protein A chromatography comprising absorbing the protein to Protein A immobilized on a solid support; removing contaminants by washing the immobilized Protein A containing the absorbed protein with a buffer comprising one or more chaotropic agents in combination with one or more hydrophobic modifiers and having a pH of at least 7.0; and eluting the protein from the Protein A immobilized on the solid support.

Within the present invention are buffers including phosphate buffer, Tris buffer, acetate buffer and citrate buffer. The invention also includes pH ranges of between 7.0 to about 10.0, about 8.0 to about 10.0 and from about 9.0 to about 10.0

Within certain embodiments chaotropic agents are selected from urea, sodium thiocynate, and guanidinium hydrochloride and hydrophobic modifiers are selected from organic solvents including ethanol, methanol, isopropanol; alkyl glycols including ethylene glycol; propylene glycol; hexaethylene glycol; and detergents including polysorbates.

Within further embodiments the buffer comprises an agent that reduces electrostatic interactions including salts such as sodium salts, potassium salts, ammonium salts, citrate salts, calcium salts and magnesium salts.

Within other embodiments contaminants are Chinese Hamster Ovary cell proteins, solid support is agarose and proteins are antibodies or antibody fragment comprising at least the CH2 and CH3 domains and Fc-fusion proteins.

Within yet other embodiments are provided a method for purifying a protein from a contaminated solution by Protein A chromatography comprising absorbing the protein to Protein A immobilized on a solid support, removing contaminants by washing the immobilized Protein A containing the absorbed protein with a wash buffer comprising about 10% isopropanol and about 1M to about 3M urea and having a pH of about 9.0; and eluting the protein from the Protein A immobilized on the solid support. Methods wherein the wash buffer comprises about 10% isopropanol and about 1M to about 3M urea and having a pH of about 9.0. Methods where the buffer comprises 2M urea and 500 mM sodium thiocynate. Methods where the buffer comprises 2M urea and 10% propylene glycol. Methods where the buffer comprises 10% isopropanol and 1M to 3M urea and 1% Tween 80. Methods where the buffer comprises 2M urea and 1% Tween 80.

Typically Protein A affinity chromatography begins with a column comprising Protein A immobilized on a solid support and equilibrated to a neutral pH with an equilibration buffer. Equilibration buffer is used to prepare the solid support for loading with the protein solution of interest. The equilibration buffer is preferably isotonic and commonly has a pH in the range from about pH 6 to about 8.

Cell culture harvest medium or other solutions containing a protein of interest in addition to other contaminants are loaded directly onto the Protein A column followed by a preliminary wash with several column volumes of equilibration buffer to remove unbound contaminants.

An intermediate wash step follows to remove contaminants that are nonspecifically bound to the solid phase or as described herein to the protein of interest, without significantly eluting the protein of interest from the solid phase. Buffer formulations used in the intermediate wash step typically have an intermediate pH in addition a low salt formulation similar to that of the elution buffer.

Often the intermediate wash step is followed by a pre-elution wash with several column volumes of buffer. The protein of interest is then eluted from the Protein A column using an elution buffer which is typically formulated at a low pH to disrupt the interactions between Protein A and the protein of interest.

Attempts have been made to make the intermediate wash step more effective in removing contaminants away from the protein of interest. The wash buffer used for the intermediate wash step is typically formulated at a pH between the load buffer and the elution buffer (i.e. an intermediate to low pH).

This pH range is selected to desorb the greatest quantity of impurities while keeping the protein of interest bound to the column and thereby preserving yield. However, lowering the pH of the wash buffer may not be sufficient to eliminate contaminants that selectively bind to the protein of interest, instead of the Protein A support matrix. Addition of mobile phase additives to aid in the disruption of interactions between the contaminants and the protein of interest brings the risk of product loss due to the weakening of the protein product—Protein A interactions in buffers having a pH that approaches those used under elution conditions.

Wash buffer formulations used to remove host cell proteins that interact with the hydrophobic controlled pore glass (CPG) stationary phase backbone on a Prosep As resin have recently been disclosed. Blank (U.S. Pat. Nos. 6,127,526 and 6,333,398) discloses Tris-based intermediate wash buffers employing hydrophobic electrolytes such as tetra methyl ammonium chloride (TMAC) and tetraethylammonium chloride (TEAC) at pH 5.0 and 7.1. Breece et al., (U.S. Pat. No. 6,870,034) provide comparisons of various Tris-based wash buffers employing combinations of polysorbate and NaCl, $Na_2SO_4$ and citrate; PEG and NaCl; Tween 20 and NaOAc; as well as 2,2-thiodiglycol, propylene glycol, hexylene glycol and urea used alone. In all cases the buffer formulations were either at pH 5.0 or 7.0. Breece et al. concluded that a lower pH resulted in less CHOP contamination in eluates from ProSepA® resins and the preferred pH was about 5.

Removing contaminants that selectively bind to the protein of interest can be more challenging. As described in the Examples below, a greater portion of CHO host cell protein contaminants (CHOP) were found to be complexed with the protein product and not associated with the agarose-based stationary phase which differs from that seen during similar protein purifications using Protein A immobilized to silica or glass stationary phases where more contaminants were associated with the stationary phase materials.

To develop a more efficient intermediate wash buffer attention was paid to disrupting the association between the contaminants and the protein of interest. The Examples provided below describe wash buffers formulated with one or more chaotropic agents that relax protein structure in combination with one or more hydrophobic modifiers to disrupt interactions between the contaminants and the protein product. Such combinations may also include agents agent that reduces electrostatic interactions. Buffers were first formulated with intermediate to low pH. The results showed that under these conditions there was a tradeoff between contaminant reduction and protein yield when using agarose-based Protein A chromatography. As discussed above, wash buffers having intermediate to low pH in combination with additives such as TMAC and detergents were shown to be effective in disrupting the interaction between CHOP and the PROSEP®—A resin backbone where more contaminants were associated with the glass pore backbone (Blank, U.S. Pat. Nos. 6,127, 526 and 6,333,398 and Breece et al., U.S. Pat. No. 6,870,034).

The interaction between the Fc region and Protein A domains has been shown be largely hydrophobic (Gagnon, Protein A affinity chromatography. In: *Purification tools for monoclonal antibodies*. 1996, Validated Biosystems, Tucson, Ariz., pp. 155-198). In addition, there are highly conserved ionizable amino acid residues (e.g. His) that face each other on the Protein A and the Fc region. At low pH, these residues take on a positive charge thus repelling each other and decreasing the hydrophobic contact area between the two molecules. This results in elution of the Fc containing molecule from the Protein A ligand. Agarose-based resins have been shown to possess substantially lower hydrophobic binding (Shukla et al., *J. Chromatography A*, 827:295-310, 1998).

At high pH, the electrostatic repulsion between the protein of interest and the Protein A can be considered to be minimal. Although chaotropic agents and hydrophobic modifiers weaken the binding of the protein to Protein A, particularly when used at more effective higher concentrations, the combination of the chaotropic agents and hydrophobic modifiers when used at high pH will not be as effective in removing the protein bound to Protein A as they would be if formulated under lower pH conditions. Accordingly, as described in the Examples below, a number of high pH wash buffer formulations combining chaotropic agents and hydrophobic modifiers, as well as agents that reduces electrostatic interactions, were tested. These high pH wash buffer formulations were successful in bypassing the tradeoff between protein yield and protein purity. Buffers formulated at higher pH enabled the product to remain bound to the Protein A and permitted an increase in the concentration of hydrophobic modifiers and chaotropic agents in the wash buffer thereby improving the removal of contaminants from the protein of interest.

Wash buffer formulations described herein include components such as chaotropic agents, hydrophobic modifiers and agents that reduce electrostatic interactions. Chaotropic agents are protein denaturants that dissociate hydrogen bonds and affect the tertiary structure of the proteins. Chaotropic agents cause destabilization of protein structure and cause unfolding. Representative chaotropic agents include, but are not limited to, urea, guanidinium hydrochloride, and sodium thiosulfate. Urea is a preferred chaotropic agent. Urea is a hydrogen bond breaker and denatures proteins at higher concentrations of >2M, although it has been shown to actually stabilize protein structure at low to moderate concentrations (Bhuyan, *Biochemistry*, 41:13386-13394, 1998). With respect to wash buffer formulations with higher pH, preferred urea concentrations range from less than 0.1M to about 3M. Some chaotropic agents may also act as hydrophobic interaction modifiers and/or agents that reduce electrostatic interactions In addition, wash buffer formulations described herein also include one or more agents that decrease hydrophobic interactions. Such hydrophobic modifiers reduce the strength of hydrophobic interactions. Hydrophobic modifiers work by directly competing for hydrophobic sites or by influencing the solution properties to reduce hydrophobic interactions. Such hydrophobic modifiers include, but are not limited to, organic solvents, alkyl glycols and detergents. Some of these hydrophobic modifiers may also act as chaotropic agents and/or agents that reduce electrostatic interactions.

Organic solvents have been shown to reduce hydrophobic interactions (Melander and Horvath, *Arch. Biochem. Biophys.*, 183:200-215, 1977). Organic solvents influence hydrophobic interactions by altering the solution properties to reduce hydrophobic interactions. Organic solvents include, but are not limited to, ethanol, methanol, and isopropanol. Wash buffer formulations are contemplated comprising one or more organic solvents at concentrations less than 1% to about 20%. An exemplary organic solvent is isopropanol, preferably about 10% to about 20% isopropanol.

Detergents are examples of hydrophobic modifiers that act by competing for hydrophobic sites and include, but are not limited to, nonionic surfactants such as polysorbates (Polysorbate 20 (Tween 20) and Polysorbate 80 (Tween 80); Triton; sodium docecyl sulfate (SDS); sodium laurel sulfate; poloxamers (poloxamer 188); sodium octyl glycoside, laurylmyristyl-, linoleyl- or steryl-sarocinsine; linoleyl-. Myristyl- or cetyl-betine; lauroamidoproply-, cocamidopropyl- or isosteramidopropyl-betaine; myristamidopropyl-, palmidopropyl-, or isosteramidopropyl-dimethylamine; sodium methyl cocoyl-, or disodium methyl oleyl-taurate; MONAQUAT™ N-lauroylsarcosine, or Nonidet P-40. Wash buffer formulations are contemplated comprising one or more detergents at less than 0.01% to about 5.0%. An exemplary detergent is Tween 80, preferably about less than 0.01% to about 2.0% Tween 80.

Wash buffer formulations of the present invention are also contemplated that include hydrophobic modifiers such as alkyl glycols. Alkyl glycols include, but are not limited to, polyethyl glycol; polypropyl glycol and hexaethylene glycol. Wash buffers are contemplated comprising one or more alkyl glycols at less than 0.1% to about 20%. An exemplary alkyl glycol is polypropyl glycol, preferably 10% polypropyl glycol.

Wash buffer formulations are also contemplated that include agents that reduce electrostatic interactions. Agents that reduce electrostatic interactions include, but are not limited to, salts. Suitable salts include, but are not limited to, phosphate, citrate, calcium, magnesium, sulfate, sodium chloride, potassium chloride, ammonium chloride, sodium acetate, potassium acetate, ammonium acetate, and sodium sulfate. Wash buffer formulations are contemplated comprising one or more salts at less than 0.05M to about 2.0M. An exemplary salt is NaCl, preferably 100 mM NaCl.

As used herein, a buffer is a buffered solution that resists changes in pH by the action of its acid-base conjugate components. Suitable buffers include, but are not limited to, phosphate buffers, Tris buffers, acetate buffers, and/or citrate buffers. Such buffers concentrations are preferably between about 1 mM and 100 mM, exemplarily buffers are between 5 mM to 25 mM. An exemplary buffer is 25 mM Tris.

Wash buffer formulations having a high pH are contemplated. Such buffers have a pH of at least 7.0 to about 12.0, at a pH at least 8.0 to about 10.0, at a pH at least 9.0 to about 10.0. Exemplary high pH buffers include those having a pH of at least 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9 or 12.0.

Any or all chromatographic steps of the invention can be carried out by any mechanical means. Chromatography may be carried out in a column. The column may be run with or without pressure and from top to bottom or bottom to top. The direction of the flow of fluid in the column may be reversed during the chromatography process. Chromatography may also be carried out using a batch process in which the solid support is separated from the liquid used to load, wash, and elute the sample by any suitable means, including gravity, centrifugation, or filtration. Chromatography may also be carried out by contacting the sample with a filter that absorbs or retains some molecules in the sample more strongly than others.

Recombinant methods for producing proteins such as antibodies or Fc fusion proteins begin with the isolated nucleic acid of desired protein. A nucleic acid encoding the protein can be directly synthesized by methods of in vitro oligonucleotide synthesis known in the art. Alternatively, smaller fragments can be synthesized and joined to form a larger fragment using recombinant methods known in the art. Polypeptides or peptide fragments may be prepared by cleavage of the intact protein, e.g. by protease or chemical cleavage. Alternatively, a truncated gene can be designed.

DNAs encoding the protein of interest can be obtained by standard molecular biology techniques (e.g., PCR amplification, site directed mutagenesis) and can be inserted into expression vectors such that the genes are operatively linked to transcriptional and translational regulatory sequences. Nucleic acids encoding the protein of interest can be cloned into a suitable expression vector and expressed in a suitable host. Suitable systems for expression can be determined by those skilled in the art. Expression vectors include plasmids, retroviruses, cosmids, YACs, EBV derived episomes, and the like. In some embodiments, the expression vectors are split DHFR vectors, PDC323 or PDC324; see, McGrew and Bianchi, "Selection of cells expressing heteromeric proteins", U.S. Patent Application No. 20030082735, 2002; and Bianchi and McGrew, *Bioengineering and Biotechnology*. 84 (4): 439-444, 2003.

Nucleic acids comprising polynucleotides of the present invention can be used in transfection of a suitable mammalian or non-mammalian host cells. Host cells are cells that can be used to express a nucleic acid, e.g., a nucleic acid encoding and antibody or Fc-fusion protein. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., *Cell* 23:175, 1981), L cells, C127 cells, 3T3 cells (ATCC CCL 163), Chinese hamster ovary (CHO) cells or their derivatives such as Veggie CHO and related cell lines which grow in serum-free media (see Rasmussen et al., *Cytotechnology* 28:31, 1998) or CHO strain DX-B11, which is deficient in DHFR (see Urlaub et al., *Proc. Natl. Acad. Sci. USA* 77:4216-20, 1980), HeLa cells, BHK (ATCC CRL 10) cell lines, the CV1/EBNA cell line derived from the African green monkey kidney cell line CV1 (ATCC CCL 70) (see McMahan et al., *EMBO J.* 10:2821, 1991), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transfected with a polypeptide-encoding nucleic acid, which can then be expressed in the host cell.

Preferred mammalian host cells include Chinese Hamster Ovary (CHO cells) (including dhfr-CHO cells, described in Urlaub and Chasin, *Proc. Natl. Acad. Sci. USA* 77:4216-4220, 1980, used with a DHFR selectable marker, e.g., as described in Kaufman and Sharp, *Mol. Biol.* 159:601-621, 1982), NS/0 myeloma cells, COS cells and SP2.0 cells. In particular for use with NS/0 myeloma cells, another preferred expression system is the GS gene expression system disclosed in WO 87/04462, WO 89/01036 and EP 338841. When expression vectors of the invention are introduced into mammalian host cells, the antibodies or antigen binding regions are produced by culturing the host cells in the appropriate culture media for a period of time sufficient to allow for expression of the antibody or antigen binding region in the host cells or, more preferably, secretion of the antibody or antigen binding region into the culture medium in which the host cells are grown.

The term transfection encompasses a wide variety of techniques commonly used for the introduction of exogenous DNA into a prokaryotic or eukaryotic host cell, e.g., electroporation, calcium-phosphate precipitation, DEAE-dextran transfection and the like. Expression eukaryotic cells, most preferably in mammalian host cells, is the most typical for antibody and immunoglobulin expression are more likely than prokaryotic cells to assemble and secrete a properly folded and immunologically active antibody or Fc fusion protein.

Once expressed, the proteins may be purified for isolation by one or more standard methods in the art, including HPLC purification, fraction column chromatography, gel electrophoresis and the like (see, e.g., Scopes, *Protein Purification*, Springer-Verlag, NY, 1982). In certain embodiments, polypeptides are purified using chromatographic and/or electrophoretic techniques. Exemplary purification methods include, but are not limited to, precipitation with ammonium sulphate; precipitation with PEG; immunoprecipitation; heat denaturation followed by centrifugation; chromatography, including, but not limited to, affinity chromatography (e.g., Protein-A-Sepharose), ion exchange chromatography, exclusion chromatography, and reverse phase chromatography; gel filtration; hydroxyapatite chromatography; isoelectric focusing; polyacrylamide gel electrophoresis; and combinations of such and other techniques. In certain embodiments, a polypeptide is purified by fast protein liquid chromatography or by high-pressure liquid chromatography (HPLC).

The antibodies contemplated for use in the invention include those directed against antigens derived from proteins of interest. Examples of proteins of interest are provided below. Recombinant fusion proteins comprising at least one constant antibody immunoglobulin domain plus all or part of one of the following proteins or their ligands or a protein substantially similar to one of these are also contemplated.

Some proteins contemplated for use in preparing antibodies or fusion proteins described herein include a flt3 ligand (International Application No. WO 94/28391), a CD40 ligand (U.S. Pat. No. 6,087,329), erythropoietin, thrombopoeitin, calcitonin, Fas ligand, ligand for receptor activator of NF-kappa B (RANKL), tumor necrosis factor (TNF)-related apoptosis-inducing ligand (TRAIL, WO 97/01633), thymic stroma-derived lymphopoietin, granulocyte colony stimulating factor, granulocyte-macrophage colony stimulating factor (GM-CSF, Australian Patent No. 588819), mast cell growth factor, stem cell growth factor, epidermal growth factor, RANTES, growth hormone, insulin, insulinotropin, insulin-like growth factors, parathyroid hormone, interferons, nerve growth factors, glucagon, interleukins 1 through 18, colony stimulating factors, lymphotoxin-β, tumor necrosis factor (TNF), leukemia inhibitory factor, oncostatin-M, and various ligands for cell surface molecules ELK and Hek (such as the ligands for eph-related kinases or LERKS).

Such protein candidates for antibody or fusion protein production also include receptors for any of the above-mentioned proteins or proteins substantially similar to such receptors. These receptors include: both forms of TNFR (referred to as p55 and p75), Interleukin-1 receptors types I and II (as described in EP Patent No. 0 460 846, U.S. Pat. No. 4,968,607, and U.S. Pat. No. 5,767,064), Interleukin-2 receptor, Interleukin-4 receptor (as described in EP Patent No. 0 367 566 and U.S. Pat. No. 5,856,296), Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK, as described in U.S. Pat. No. 6,271,349), receptors for TRAIL (including TRAIL receptors 1, 2, 3, and 4), and receptors that comprise death domains, such as Fas or Apoptosis-Inducing Receptor (AIR).

Other proteins for antibody or fusion protein production include differentiation antigens (referred to as CD proteins) or their ligands or proteins substantially similar to either of these, which are fused to at least one constant antibody immunoglobulin domain, optionally an Fc portion of an antibody. Such antigens are disclosed in *Leukocyte Typing VI (Proceedings of the VIth International Workshop and Conference*, Kishimoto, Kikutani et al., eds., Kobe, Japan, 1996). Similar CD proteins are disclosed in subsequent workshops. Examples of such antigens include CD27, CD30, CD39, CD40, and ligands thereto (CD27 ligand, CD30 ligand, etc.). Several of the CD antigens are members of the TNF receptor family, which also includes 41BB ligand and OX40. The ligands are often members of the TNF family, as are 41BB ligand and OX40 ligand. Accordingly, members of the TNF and TNFR families can also be purified using the present invention.

Enzymatically active proteins are contemplated for antibody or fusion protein production as well. Such proteins include metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, ligands for any of the above-mentioned enzymes, and numerous other enzymes and their ligands.

The method of the invention may also be used to purify conjugates comprising an antibody and a cytotoxic or luminescent substance. Such substances include: maytansine derivatives (such as DM1); enterotoxins (such as a Staphlyococcal enterotoxin); iodine isotopes (such as iodine-125); technium isotopes (such as Tc-99m); cyanine fluorochromes (such as Cy5.5.18); and ribosome-inactivating proteins (such as bouganin, gelonin, or saporin-S6). Examples of antibodies or antibody/cytotoxin or antibody/luminophore conjugates contemplated by the invention include those that recognize any one or combination of the above-described proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, L-4, IL-5, IL-8, IL-10, IL-2 receptor, IL-4 receptor, IL-6 receptor, IL-13 receptor, IL-18 receptor subunits, PDGF-β, VEGF, TGF, TGF-β2, TGF-β1, EGF receptor, VEGF receptor, C5 complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, IFN-γ, Respiratory Syncitial Virus, human immunodeficiency virus (HIV), hepatitis B virus (HBV), *Streptococcus mutans*, and *Staphylococcus aureus*.

Also contemplated are anti-idiotypic antibodies, or substantially similar proteins, including but not limited to anti-idiotypic antibodies against: an antibody targeted to the tumor antigen gp72; an antibody against the ganglioside GD3; or an antibody against the ganglioside GD2.

The present invention, thus generally described, will be understood more readily by reference to the following examples, which are provided by way of illustration and are not intended to be limiting of the present invention.

EXAMPLES

Example 1

This experiment provides details regarding the chromatographic behavior of Chinese Hamster Ovary Protein contaminants (CHOP) present in CHO cell culture harvest supernatant with and without a spiked antibody product to determine if CHOP interacts with the Protein A backbone material or if it directly interacts with protein product bound to the Protein A. CHO cell culture harvest supernatant was prepared from untransfected CHO cells (the null supernatant). The "spiked" supernatant was prepared by adding purified monoclonal antibody to the OX40 ligand (Khare et al., WIPO International Publication No. WO 05/094879) at a concentration of ~1 mg/ml to the null supernatant, incubated overnight. The null and spiked supernatants were then loaded onto Protein A immobilized on two different types of supports: an agarose-base support (MAbSelect™, Amersham Biosciences, Uppsala, Sweden) and a pore glass matrix (Prosep A®, Millipore, Billerica, Mass.). The columns were then subjected to a wash combination of equilibration buffer (3 column volumes (CV) 25 mM Tris, 100 mM NaCl, pH 7.4), an intermediate wash (3CV of 50 mM citrate, pH 4.4) and then eluted with (100 mM acetate, pH 3.6). The column effluent during the elution phase was collected and analyzed for CHOP by ELISA.

CHOP was detected in the elution portion from both the null and spiked supernatants collected from the Prosep A® resin indicating that CHOP binds to both the Protein A backbone material as well as the bound antibody species. However, very low levels of CHOP were detected in the elution portion of the null supernatant compared to the spiked supernatant collected from the MAbSelect™ resin. Based on these results it appears that CHOP does not bind independently to agarose-based Protein A resins to the degree that it binds to controlled pore glass-based Protein A resins. This is in agreement with observations made in U.S. Pat. Nos. 6,127,526 and 6,333,398 in which significant hydrophobic interactions were implicated in CHOP binding to the Prosep A® CPG backbone. When purified monoclonal antibody was spiked into the null supernatant and employed as the column load, significantly higher levels of CHOP were observed during elution on MAbSelect™ as well as Prosep A®. CHOP association with the protein product is responsible for elevated CHOP levels being present in Protein A chromatography. Therefore, development of a generic wash buffer should focus on disrupting the association between the desired protein product and the host cell protein impurities rather than the interaction between the host cell impurities and the Protein A resin backbone.

Example 2

Protocols for protein purification using MAbSelect™ Protein A columns typically require the intermediate wash to have a pH somewhere between that of the equilibration buffer and of the elution buffer. The buffer formulation and pH are independently determined for each protein to be purified. A generic intermediate wash buffer that could be used effectively during purification of a wide range of proteins would eliminate this need. Also, described in Example 1, CHOP was found to associate with the protein of interest when purified on agarose-based Protein A resins, compared to glass resins where more CHOP was associated with the resin backbone. There is a need for buffers that can reduce the association of contaminants and the protein of interest. Accordingly, a series of experiments were carried out to compare the effectiveness of various wash buffer formulations. MAbSelect™ Protein A columns were prepared according to manufacturer's directions. The columns were loaded with CHO cell culture harvest supernatant spiked with an OX40L monoclonal antibody. A control experiment was carried out involving an extended wash with equilibration buffer (25 mM Tris, 100 mM NaCl, pH 7.4) followed by a pre-elution wash (3CV of 50 mM citrate, pH 4.4) and compared to the wash combination of equilibration buffer (3CV of 25 mM Tris, 100 mM NaCl, pH 7.4), an intermediate wash using one of the buffer formulations listed in Table 1, followed by pre-elution buffer (3CV of 50 mM citrate, pH 4.4) and elution of the antibody.

Table 1 lists the composition of the intermediate washes as well as the normalized CHOP and yield values. For each of the buffer formulations tested the step yield and eluate CHOP value were normalized to the values obtained for the control sample. The buffers were either Tris or citrate-based. The buffer formulations consisted of chaotropic agents; hydrophobic modifiers such as organic solvents; salts and tetramethylammonium chloride (TMAC). The pH range of the buffers was between 4.4 and 6.0. Among the buffer formulations that were effective in washing out CHOP (~50% of control) were 1M urea alone or in combination with 100 mM NaCl and 20% isopropanol, all at pH 4.4. However, in all of these cases the step yield was significantly lower than that for the control experiment, indicating that in addition to removing CHOP, these formulations weakened the interaction between the antibody and Protein A resulting in premature release of the antibody from the Protein A. The outcome of these experiments indicate that formulations independently consisting of chaotropic agents or hydrophobic modifiers, at intermediate to low pH result in a trade-off between yield and purity, see FIG. 1a and Table 1. The desired outcome was buffer formulations where contaminant levels were reduced while minimizing loss of the desired protein.

TABLE 1

Intermediate wash buffer formulations <6.0 Normalized CHOP and yield values as compared to a control elution

| Intermediate Wash Buffer Formulation | Yield (normalized to control) | CHOP in eluate (normalized to control) |
|---|---|---|
| Control | 100 | 100 |
| 25 mM Tris, pH 9.0 | 101 | 104 |
| 50 mM citrate, 1M urea, pH 4.4 | 82 | 49 |
| 50 mM citrate, 10% propylene glycol, pH 4.4 | 95 | 101 |

TABLE 1-continued

Intermediate wash buffer formulations <6.0 Normalized
CHOP and yield values as compared to a control elution

| Intermediate Wash Buffer Formulation | Yield (normalized to control) | CHOP in eluate (normalized to control) |
|---|---|---|
| 50 mM citrate, pH 4.4 | 97 | 104 |
| 50 mM citrate, pH 4.2 | 85 | 88 |
| 50 mM citrate, 1M urea, 100 mM NaCl, pH 4.4 | 60 | 46 |
| 50 mM citrate, 5% ethanol, pH 4.4 | 98 | 109 |
| 50 mM citrate, 5% ethanol, 100 mM NaCl, pH 4.4 | 85 | 94 |
| 50 mM citrate, 1M urea, pH 6.0 | 97 | 82 |
| 50 mM citrate, 5% isopropanol, pH 4.4 | 99 | 78 |
| 50 mM citrate, 0.5M TMAC, pH 4.4 | 63 | 68 |
| 50 mM citrate, 100 mM sodium sulfate, pH 4.4 | 79 | 79 |
| 50 mM citrate, 1% Tween 80, pH 4.4 | 96 | 80 |
| 50 mM citrate, 10% isopropanol, pH 4.4 | 97 | 108 |
| 50 mM citrate, 15% isopropanol, pH 4.4 | 98 | 90 |
| 50 mM citrate, 20% isopropanol, pH 4.4 | 75 | 27 |

Since product yield is impacted by dissociation of the protein product from the Protein A, conducting the intermediate wash under conditions where this interaction remains strong is desirable. A second set of wash buffer formulations was tested, this time allowing for higher pH conditions. At pH 9.0, the electrostatic repulsion between the antibody and Protein A should be minimal. Agents that decrease hydrophobic interactions will still weaken the binding of the protein product, however they should not be as effective as they would be under lower pH conditions. Combinations of chaotropic and hydrophobic modifiers with and without agents that reduce electrostatic interactions, were tested. The buffer formulations and resulting normalized yield and CHOP data from these experiments is shown in Table 2 below.

The high pH buffer formulations comprising at least one chaotropic agent and at least one hydrophobic modifier were successful in bypassing the trade-off between yield and purity that was observed with the previous wash buffers shown in Table 1. In those experiments, buffer formulations consisting of only urea or isopropanol independently were not as effective, for instance, as the combination of urea and isopropanol at high pH as shown in Table 2. The further addition of agents that reduce electrostatic interactions also improved the buffer effectiveness. CHOP levels in the eluates decreased substantially without significant deleterious effect on product yield; see FIG. 1b and Table 2.

Table 3 shows the results when various high pH buffer formulations consisting of a chaotropic agent and a hydrophobic modifier were tested. In all cases the yield remained high and CHOP values declined.

The combination of washing the column using a buffer having a high pH allowed the antibody product to remain bound to the column, while the concentration of the hydrophobic modifiers and chaotropic agents in the wash buffer could be increased to successfully disengage CHOP from the antibody product.

TABLE 2

Intermediate wash buffer formulations Normalized CHOP
and yield values as compared to a control elution

| Intermediate wash | Yield (normalized to control) | CHOP in eluate (normalized to control) |
|---|---|---|
| Control | 100 | 100 |
| 25 mM Tris, pH 9.0 | 97 | 87 |
| 25 mM Tris, 1M urea, pH 9.0 | 98 | 83 |
| 25 mM Tris, 10% isopropanol, pH 9.0 | 101 | 73 |
| 25 mM Tris, 10% isopropanol, 1M urea, pH 9.0 | 98 | 68 |
| 25 mM Tris, 10% isopropanol, 2M urea, pH 9.0 | 103 | 54 |
| 25 mM Tris, 10% isopropanol, 3M urea, pH 9.0 | 100 | 41 |
| 25 mM Tris, 10% isopropanol, 1M urea, 1% Tween 80, pH 9.0 | 97 | 63 |
| 25 mM Tris, 10% isopropanol, 2M urea, 1% Tween 80, pH 9.0 | 99 | 61 |
| 25 mM Tris, 10% isopropanol, 3M urea, 1% Tween 80, pH 9.0 | 102 | 40 |
| 25 mM Tris, 2M urea, 10% propylene glycol, pH 9.0 | 102 | 46 |
| 25 mM Tris, 2M urea, 500 mM sodium thiocyanate, pH 9.0 | 93 | 37 |
| 25 mM Tris, 2M urea, 1% Tween 80, pH 9.0 | 99 | 48 |

TABLE 3

Intermediate wash buffer formulation over a pH range Normalized
CHOP and yield values as compared to a control elution

| Intermediate wash | Yield (normalized to control) | CHOP in eluate (normalized to control) |
|---|---|---|
| 25 mM Tris, 10% isopropanol, 2M urea, pH 9.0 | 103 | 54 |
| 25 mM Tris, 10% isopropanol, 2M urea, pH 8.0 | 109 | 65 |
| 25 mM phosphate, 10% isopropanol, 2M urea, pH 7.0 | 107 | 67 |

Example 3

The above experiments were carried out using material from a single lot of cell culture harvest fluid expressing an OX40L monoclonal antibody. To test the generality of the observations made in the above, four different cell culture harvest lots of the OX40L monoclonal antibody were loaded onto MAbSelect™ Protein A columns as described above. The intermediate wash buffer formulation: 25 mM Tris, 10% isopropanol, 1M urea, pH 9.0, was used. For each lot a control experiment was carried out involving an extended wash with equilibration buffer (25 mM Tris, 100 mM NaCl, pH 7.4) followed by a pre-elution wash (3CV of 50 mM citrate, pH 4.4) and compared to the wash combination of equilibration buffer (3CV of 25 mM Tris, 100 mM NaCl, pH 7.4), an intermediate wash (25 mM Tris, 10% isopropanol, 1M urea, pH 9.0), followed by pre-elution buffer (3 CV of 50 mM citrate, pH 4.4) and elution of the antibody, The normalized CHOP and yield data are shown in Table 3. As can be seen in Table 3, the 25 mM Tris, 10% isopropanol, 1M urea, pH 9.0 intermediate wash buffer formulation successfully reduced CHOP to ~half that detected in the control experiment and maintained high product yield among all of the different lots.

TABLE 4

Comparison of CHOP and Yield values between various cell culture harvest lots

| Cell culture harvest lot number | Yield (normalized to control) | CHOP in eluate (normalized to control) |
|---|---|---|
| Control | 100 | 100 |
| Lot 1 | 128 | 40 |
| Lot 2 | 112 | 67 |
| Lot 3 | 113 | 42 |
| Lot 4 | 113 | 39 |

To determine the generic nature of these intermediate wash buffer formulations for use in Protein A chromatography of such diverse proteins such as monoclonal antibodies and Fc fusion proteins, a representative intermediate wash buffer from above was tested to determine the effectiveness of such wash buffer formulations on the elution and recovery of several different proteins. Four proteins were selected including an $IgG_1$ monoclonal antibody, two different $IgG_2$ monoclonal antibodies and an Fc fusion protein with an $IgG_1$.

Four combinations of post-load washes were employed to test the efficacy of the wash buffer formulation formulations having chaotropic agents in combination with hydrophobic modifiers at high pH.

I: 3CV equilibration buffer wash followed by a specific intermediate pH wash buffer formulation for the molecule.

II: 3 CV equilibration buffer wash followed by the intermediate wash buffer described herein followed by 3 CV of the specific wash.

III: extended wash with equilibration buffer only.

IV: 3 CV equilibration buffer followed by the intermediate wash (3CV) and finally 3 CV of equilibration buffer.

The combinations II and IV used the 25 mM Tris, 10% isopropanol, 1M urea, pH 9.0 wash buffer and combinations I and III represent the controls.

TABLE 5

Evaluation of the intermediate wash for several monoclonal antibodies and Fc fusion protein

| Wash | CHOP in eluate (normalized to control) | Yield (normalized to control) | Wash | CHOP in eluate (normalized to control) | Yield (normalized to control) |
|---|---|---|---|---|---|
| | IgG2 | | | IgG1 | |
| I | 74 | 91 | I | 31 | 77 |
| II | 30 | 93 | II | 22 | 86 |
| III | 100 | 100 | III | 100 | 100 |
| IV | 22 | 99 | IV | 26 | 99 |
| | IgG2 | | | Fc Fusion Protein | |
| I | 66 | 96 | I | 65 | 98 |
| II | 35 | 102 | II | 26 | 90 |
| III | 100 | 100 | III | 100 | 100 |
| IV | 45 | 101 | IV | 23 | 93 |

Table 5 shows the CHOP and yield data from these four proteins. As can be seen from the Table, use of the intermediate wash buffer gave product yields in the same range as the control experiments. However, CHOP numbers were the lowest for combinations II and IV across all four proteins indicating that a generic intermediate wash buffer formulation that maintains high product yields while reducing CHOP, but the yield was comparable to combinations I and III.

Clearly, the strategy of moving to a higher pH range to allow for the usage of higher concentrations and combinations of wash additives was a successful strategy in that it allows the use of this wash for a variety of CHO expressed molecules without the need for significant development effort for each molecule. In addition, this wash is expected to be applicable for the purification of this class of molecules on all Protein A chromatographic stationary phases irrespective of the resin backbone. The development of a generic wash step for purification on agarose based Protein A resins represents a significant advance over the current paradigm of process development on these media.

The invention claimed is:

1. A method for purifying an IgG1 or IgG2 antibody from a solution containing at least one contaminant by Protein A chromatography comprising:

a) absorbing the IgG1 or IgG2 antibody to Protein A immobilized on a solid support;

b) removing contaminants by washing the immobilized Protein A containing the absorbed IgG1 or IgG2 antibody with a wash buffer comprising 25 mM Tris, 1M to 3M urea, and an organic solvent selected from 10% (v/v) isopropanol or 10% (w/v) propylene glycol, and wherein said wash buffer has a pH of at least 9.0; and c) eluting the IgG1 or IgG2 antibody from the Protein A immobilized on the solid support.

2. The method according to claim 1, wherein the selected organic solvent is 10% (v/v) isopropanol.

3. The method according to claim 1, wherein the selected organic solvent is 10% (w/v) propylene glycol.

4. The method according to claim 1, wherein said at least one contaminant is Chinese Hamster Ovary cell proteins.

5. The method according to claim 1, wherein said solid support is agarose.

* * * * *